United States Patent [19]

Slocum

[11] Patent Number: 4,955,888
[45] Date of Patent: Sep. 11, 1990

[54] BIRADIAL SAW

[76] Inventor: D. Barclay Slocum, 241 Spy Glass Dr., Eugene, Oreg. 97401

[21] Appl. No.: 383,722

[22] Filed: Jul. 24, 1989

[51] Int. Cl.$^5$ .......................... A61B 17/00; A61F 5/00
[52] U.S. Cl. ...................................... 606/82; 606/176; 606/178
[58] Field of Search ................. 606/82, 171, 176, 177, 606/178, 179, 180; 30/301, 316, 317, 248, 304; 128/305; D7/43, 106

[56] References Cited

U.S. PATENT DOCUMENTS

| | | | |
|---|---|---|---|
| 1,619,619 | 3/1927 | Kyfes | 30/317 |
| 2,412,149 | 12/1946 | Higgins | 30/304 |
| 2,455,655 | 12/1948 | Carroll | 606/178 |
| 2,702,550 | 2/1955 | Rowe | 606/178 |
| 3,515,128 | 6/1970 | McEvoy | 30/130 |
| 3,554,197 | 1/1971 | Dobbie | 606/178 |
| 4,150,675 | 4/1979 | Comparetto | 606/85 |
| 4,409,973 | 10/1983 | Neufeld | 606/178 |
| 4,513,742 | 4/1985 | Arnegger | 606/178 |
| 4,708,133 | 11/1987 | Comparetto | 606/177 |

*Primary Examiner*—Robert A. Hafer
*Assistant Examiner*—Michael Brown
*Attorney, Agent, or Firm*—Kolisch, Hartwell & Dickinson

[57] ABSTRACT

A biradial saw including a biradial saw blade having an elongate, arcuate body with a cutting end that is constructed to penetrate a solid substance. The blade's body is formed with inner and outer arcuate surfaces whose curvature radii are substantially equal but oriented relative to offset axes of curvature. Also included is a means for producing oscillating motion, and a means for attaching the blade's rear end to the oscillating-motion-producing means.

11 Claims, 1 Drawing Sheet

BIRADIAL SAW

BACKGROUND AND SUMMARY OF THE INVENTION

This invention relates generally to devices that are used to make an arcuate cut through a solid substance, and more particularly to devices used to make an arcuate cut through a bone as part of an osteotomy procedure.

An osteotomy is a surgical procedure used to correct a defective bone orientation. To perform the procedure, the defectively oriented bone is severed into two matable sections, and then these sections are reoriented.

There are various types of osteotomies in which arcuate cuts are made in a bone's entire cross section. For example, in a high femoral or inter-trochanteric osteotomies, an arcuate cut is made in the entire cross section of a living subject's femur. Additionally, according to the teaching in U.S. Pat. No. 4,409,973 to Neufeld, an arcuate cut is made in the entire cross section of the subject's tibia.

Another type of osteotomy involves making an arcuate cut in only a portion of the cross section of the subject's bone. For example, as taught in U.S. Pat. No. 4,677,973 to Slocum, an arcuate cut is made in only a portion of the canine tibia, i.e. the metaphyseal region of the tibia.

In each of the above-identified osteotomies, the arcuate-cut procedure is very important, and critical to success. A key aspect of the arcuate-cut procedure is the quality of the "match" between mating surfaces formed by the cut. The better the "match", the better the bone will be supported when the surfaces are rejoined and the osteotomy is completed.

When an arcuate cut is made, it is made in a curvilinear plane through the bone, or bone portion, as in the tibial portion that is cut in the proximal tibial osteotomy disclosed in U.S. Pat. No. 4,677,973 to Slocum. Such a cut divides the bone into two mating-bone sections having corresponding mating surfaces. A key feature of the two surfaces is the radius of curvature that defines them.

In theory, the "perfect" cut would produce two mating-bone sections whose mating surfaces "match" perfectly, i.e. the two surfaces mating at an infinite number of lines in the curvilinear plane in which the cut was made. Such a perfect "match" is possible only if the two surfaces have identical radii of curvature.

Because the two surfaces' curvature radii are defined by the cylindrical saw's mating-surface-forming blade, the saw blade is an important element in the success of an osteotomy. Such a blade includes an outer cylindrical surface defined by one radius of curvature and an inner cylindrical surface defined by another radius of curvature.

Conventional cylindrical saws used in performing osteotomies are not capable of making the "perfect" cut because their saw blades have outer and inner cylindrical surfaces that are defined by different curvature radii.

An example of such a prior-art saw blade is shown in U.S. Pat. No. 4,409,973 to Neufeld. Neufeld discloses a cylindrical saw having an elongate, semi-cylindrical saw blade. The saw blade includes an outer and inner semi-cylindrical surface, the outer surface of which has a radius of curvature greater than the blade's inner surface.

Because the saw blade's surfaces have different curvature radii, mating-bone surfaces formed by the blade will only marginally mate. This is so because the mating-bone surfaces will have different curvature radii, one defined by the saw blade's outer surface and the other defined by the saw blade's inner surface.

It is therefore an object of the present invention to provide an arcuate saw blade for making an arcuate cut through a solid substance that greatly improves the conformity of the substance's cut-produced, mating surfaces.

A further object of the present invention is to provide an arcuate saw blade for use in corrective osteotomies that produces two bone sections having mating surfaces that more 10 perfectly "match", thus providing greatly increased stability to the rejoined bone sections.

A still further object of the invention so far outlined is to provide an arcuate saw blade usable to make an arcuate cut that facilitates fixation of the cut-produced, mating-bone sections relative to each other.

Yet another object of the present invention is to provide an arcuate saw blade for use in corrective osteotomies that will promote healing of the rejoined bone sections by providing an improved "match" between the bone sections' corresponding mating surfaces.

The invention described herein achieves the above-identified objects by providing a biradial saw including a biradial saw blade having an elongate, arcuate body. The body includes a cutting end, and inner and outer arcuate surfaces, each being characterized by substantially the same radius of curvature. However, the body's surfaces have different axes of curvature.

To make a desired cut in a solid substance such as a bone, the blade is oscillated about a cutting axis in the curvilinear planes of its surfaces. The cutting axis substantially parallels the surfaces axes of curvature and is located between them.

As the blade moves through the bone, it cuts the same into two sections having matable, cut-produced surfaces that more nearly have the same radii of curvature.

Because the saw blade's inner and outer surfaces have different axes of curvature, minor "shaving" of bone, or other material, will occur because, during the cutting operation, both surfaces are oscillated about the same cutting axis. The term shaving refers to an action that occurs when the cutting axis is in an off-axis position relative to either curvature axis of the blade's inner or outer surface.

To take maximum advantage of the saw of the invention, the cutting axis is offset from the inner and outer surfaces' axes of curvature. In the preferred embodiment, the cutting axis is located at an optimum offset which is substantially halfway between the surfaces' axes of curvature.

Also, to further maximize the advantage of the invention, the saw blade is oscillated through an angle of 5°–15°.

These and other advantages and objectives of the present invention will become more fully apparent as the description which follows is read in conjunction with accompanying drawings.

DETAILED DESCRIPTION OF THE INVENTION

Figure 1:
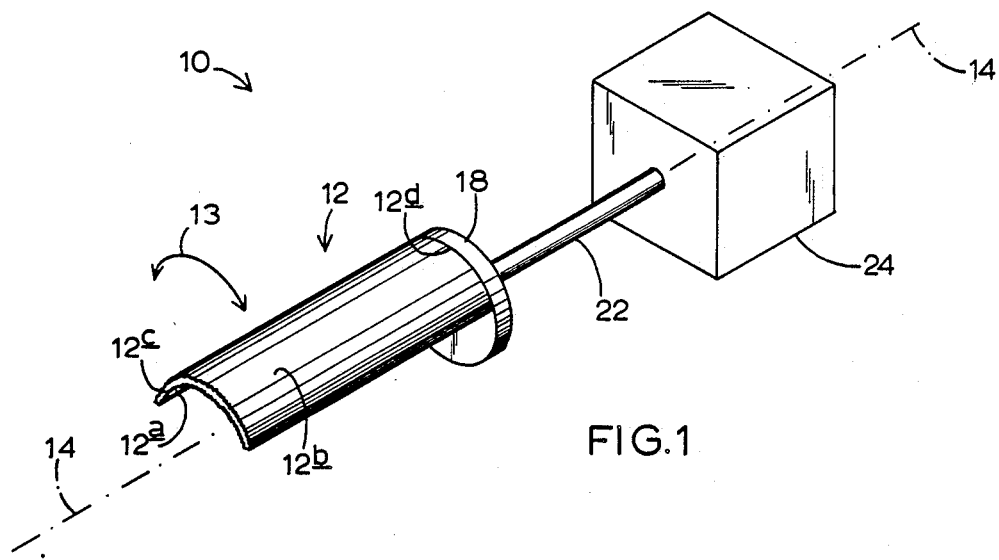
FIG. 1 is a perspective view of the biradial saw of the present invention.

In FIG. 1, a biradial saw 10 made in accordance with the present invention is shown including an arcuate biradial saw blade 12 which is a key feature of the invention. Preferably, blade 12 is made of a suitably rigid material such as steel, and for reasons soon to be described, is formed by casting.

Figure 3:
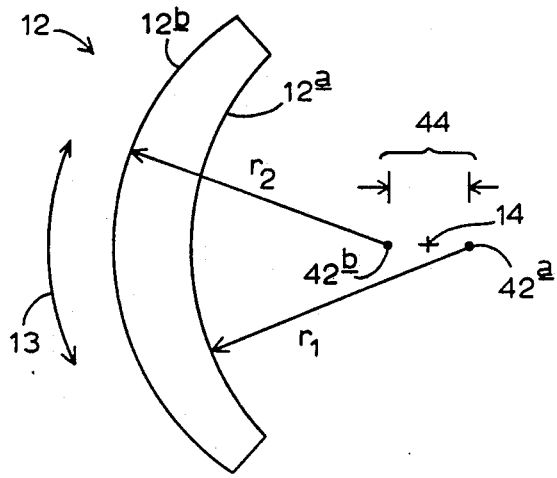
FIG. 3 is an enlarged, simplified, cutting-axis view of the saw blade which forms part of the present invention.

Blade 12 includes an inner arcuate surface 12a and an outer arcuate surface 12b, each of which will be more particularly described in the discussion of FIG. 3. Blade 12 also includes forward cutting end 12c and rear end 12d. End 12c is constructed with teeth to enable the blade to penetrate a desired solid substance, such as bone, when the blade is oscillated, as indicated by double-ended arrow 13, about a soon-to-be described cutting axis.

Continuing with FIG. 1, blade 12 is disposed about a cutting axis 14 shown by dot-dash lines. Rear end 12d of blade 12 is coupled to a circular plate 18 along the plate's perimeter. Plate 18 is connected to one end of a shaft 22 the other end of which is operatively connected to a motor, or means for producing oscillating motion, shown schematically by box 24. Axis 14 is substantially parallel to the long axis of blade 12, and is coincident with the rotational axis of shaft 22. Also, preferably, the oscillating-motion-producing means oscillates blade 12 at a rate of approximately 10,000–14,000 cycles/second.

Figure 2:
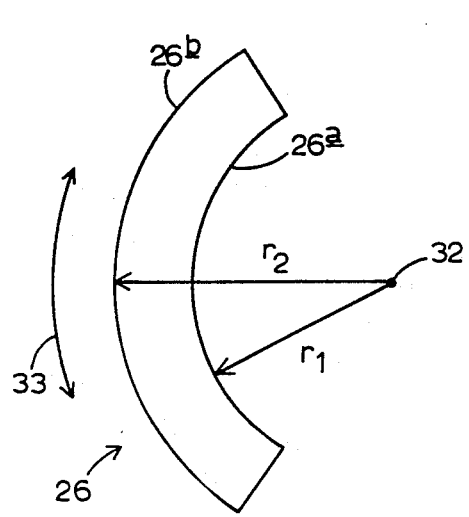
FIG. 2 is an enlarged, simplified, cutting-axis view of a prior-art cylindrical-saw blade.
Figure 2A:
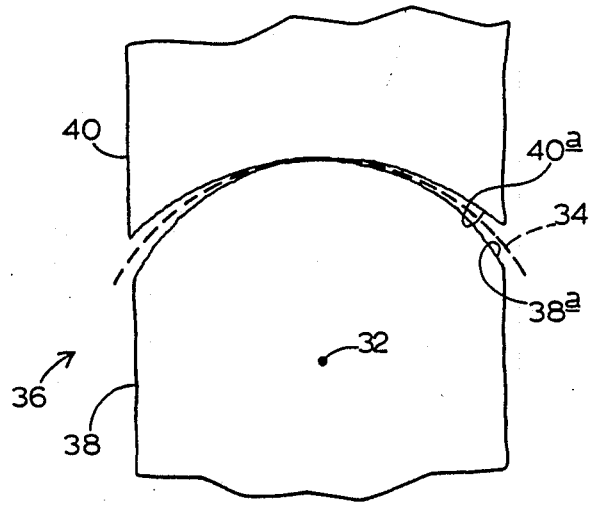
FIG. 2A is an enlarged, exaggerated view of a cut produced by the blade of FIG. 2 after the blade has cut a bone.

Turning now to FIGS. 2 and 2A, a further description of prior-art cylindrical-saw blades is provided to assist the reader in understanding the present invention. FIG. 2 shows a simplified, exaggerated cutting-axis view of a prior-art cylindrical-saw blade 26 having an inner surface 26a and an outer surface 26b.

Inner and outer surfaces 26a, 26b have the same axis of curvature 32, but have different radii of curvature. Specifically, inner surface 26a has a radius of curvature $r_1$ which is less than radius of curvature of $r_2$ of outer surface 26b. In other words, inner and outer surfaces 26a, 26b have a concentric relationship relative to each other. Thus, when blade 26 is oscillated bidirectionally along an arcuate path shown by double-ended arrow 33, it will make a cut in a solid substance, the opposite sides of which will generally match the outlines of surfaces 26a, 26b as shown.

Turning now to FIG. 2A, the effect of the above-identified concentric relationship of the prior-art cylindrical-saw blade's surfaces is shown. Briefly, such effect is to produce bone sections with cut surfaces that only marginally mate. Here, a fragmentary portion of a bone 36 is shown after blade 26 has cut through a section of the bone adjacent a curvilinear plane 34. As it cut through bone 36, the blade separated the bone into sections 38, 40 having confronting surfaces 38a, 40a.

Surface 38a has a convex shape and is formed and defined by, referring back to FIG. 2, the blade's inner surface 26a. Thus, surface 38a has substantially the same radius of curvature as inner surface 26a. Similarly, surface 40a is formed and defined by the blade's outer surface 26b, and thus has the same radius of curvature as outer surface 26b.

Still referring to FIG. 2A, the difference in the curvature radii of surfaces 38a, 40a results in the surfaces mating only in a central region of plane 34. At outer regions of plane 34 the surfaces do not mate.

As a result of surfaces 38a, 40a having different curvature radii, the same only marginally mate. Such a condition produces an unstable joint when bone sections 38, 40 are rejoined because the above-described non-mating areas of surfaces 38a, 40a (i.e. adjacent outer regions of plane 34) allow the bone sections to "rock" relative to each other.

Figure 3A:
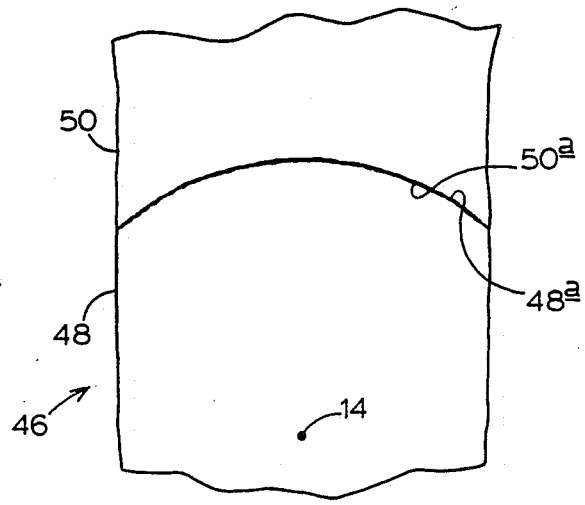
FIG. 3A is an enlarged, exaggerated view of the improved cut produced by the saw of the present invention after its blade has cut a bone.

Turning now to FIGS. 3 and 3A, the improved matability between bone sections attainable with the saw blade of the present invention is shown. In FIG. 3, an exaggerated cutting-axis view of a cutting face of blade 12 is shown including inner and outer surfaces 12a, 12b, respectively.

Surfaces 12a, 12b of the cutting face of do not have a concentric relationship relative to each other. Rather, they have the same radius of curvature. Thus, radius of curvature $r_1$ of inner surface 12a is the same as radius of curvature $r_2$ of outer surface 12b.

Because inner and outer surfaces 12a, 12b are different surfaces having substantially the same curvature radii, they must have different axes of curvature 42a, 42b, respectively. Axis 14 is located substantially halfway between axes 42a, 42b.

Still referring to FIG. 3, it is possible to describe the blade's novel structure another way. The above-described relationships of the curvature radii and curvature axes of inner and outer surfaces 12a, 12b produce the blade's unique elongate cross section, or radial dimension, or cutting face which is characterized by having a relatively wide central region and opposing tapered outer regions each having a width that is less than that of the central region. Thus, the width of each outer region diminishes relative to the width of the central region.

As can now be understood, the novel structure of blade 12 is not obtainable by bending a conventional sheet of metal because such a process would not yield a blade whose inner and outer arcuate surfaces have the same curvature radii. Rather, blade 12 is formed preferably by casting, or by machining a suitable portion of a solid cylinder of metal.

Still referring to FIG. 3, as blade 12 is oscillated bidirectionally along an arcuate path shown by arrow 13, there will be a tendency for the blade to "shave" a cut of bone sections. This is because blade 12 has two different curvature axes 42a, 42b that, referring back to FIG. 1, rock about one cutting axis 14. Thus, referring again to FIG. 3, it is impossible to oscillate the saw about a single cutting axis that is equal to both curvature axes 42a, 42b.

To minimize the "shaving" associated with the different curvature axes of inner and outer surfaces 12a, 12b, the cutting axis of blade 12 is offset relative to each of the surfaces' curvature axes. This offset range is shown generally under bracket 44. Preferably, cutting axis 14 is positioned, as mentioned earlier, so that it is substantially midway between axes 42a, 42b. Also, because "shaving" is further minimized by oscillating the blade through a relatively small angle, blade 12 is oscillated through an angle of between 5°–15°. When blade 12 is oscillated about axis 14 to cut a bone portion such as that shown at 46 in FIG. 3A, there is a surprising result.

More particularly, the resulting separated bone sections, shown at 48, 50 in FIG. 3A, end up with opposed cut surfaces, 48a, 50a respectively, which have more nearly the same radii of curvature than those obtained in cut bone sections according to prior-art techniques. As a consequence, these surfaces can mate with one another in a far more intimate manner, and such situation is shown in an exaggerated fashion in FIG. 3A.

Thus, a resulting cut using the saw of the present invention produces two bone sections having matable surfaces that achieve a significantly better "match" than that produced by prior-art blades. Such an improved "match" results in greatly improved conformity between a bone's cut-produced, mating surfaces.

Additionally, fixation of the cut-produced bone sections relative to their corresponding mating surfaces is facilitated by the mating surfaces' improved conformity relative to each other. Finally, each of the above-described conditions promotes healing of the rejoined bone sections.

Accordingly, while a preferred embodiment of the invention has been described herein, it is appreciated that variations and modifications are possible which come within the scope of the invention.

It is claimed and desired to secure by Letters Patent:

1. A biradial saw blade comprising
an elongate, arcuate body having a cutting end,
said body including inner and outer arcuate surfaces, each characterized by substantially the same radius of curvature, with each surface curving about an axis offset from the axis of the other surface, which axis substantially parallels the long axis of said body.

2. The saw blade of claim wherein said body is structured to oscillate, generally in the curvilinear planes of said surfaces about a cutting axis.

3. The saw blade of claim 2, wherein said cutting axis substantially parallels the axes of curvature of said surfaces, and is located therebetween.

4. The saw blade of claim 3, wherein said cutting axis is substantially halfway between said axes of curvature.

5. A biradial saw blade for use in corrective osteotomies, comprising:
an elongate arcuate saw body having a cutting end, said cutting end being constructed to penetrate a desired bone region,
said body including an outer arcuate surface having a first radius of curvature and an inner arcuate surface having a second radius of curvature substantially equal to said first radius, with each surface curving about an axis offset from the axis of the other surface, which axis substantially parallels the long axis of said body, and
said blade being usable to cut through the bone region, to produce two bone sections having arcuately, substantially conforming surfaces.

6. The saw blade of claim 5, wherein said body is structured to oscillate, generally in the curvilinear planes of said surfaces about a cutting axis.

7. The saw blade of claim 6, wherein said cutting axis substantially parallels the axes of curvature of said surfaces, and is located therebetween.

8. The saw blade of claim 7, wherein said cutting axis is substantially halfway between said axes of curvature.

9. A biradial saw blade comprising
an elongate arcuate body having a cutting end,
said body having a cutting face including a cross section characterized by a relatively wide central region and opposing tapered outer regions each having a width that is less than that of said central region.

10. A biradial saw blade comprising
an elongate arcuate, body having a cutting end,
said body having a cutting face including an elongate arcuate cross section having an elongate radial dimension that diminishes from a central region to the ends thereof.

11. A biradial saw comprising
an elongate arcuate saw blade including an inner arcuate surface having a first radius of curvature and an outer arcuate surface having a second radius of curvature substantially equal to said first radius, with each surface curving about an axis offset from the axis of the other surface, which axis substantially parallels the long axis of said blade,
said blade being disposed generally in the curvilinear planes of said surfaces about a cutting axis, and having a cutting end and a rear end, said cutting end being constructed to penetrate a desired solid substance,
means for producing oscillating motion,
means operatively attaching said rear end to said oscillating-motion-producing means, and
said blade being structured to be oscillated about said cutting axis by said oscillating-motion-producing means to produce a cut separating such a substance into two sections each having an arcuate, substantially matable surface, and each such matable surface having substantially the same radius of curvature.

* * * * *